United States Patent [19]

Lennox

[11] 4,292,472
[45] Sep. 29, 1981

[54] ELECTRONIC ARTIFICIAL LARYNX

[76] Inventor: Thomas M. Lennox, 7670 Acacia Ave., Mentor, Ohio 44060

[21] Appl. No.: 121,300

[22] Filed: Feb. 14, 1980

Related U.S. Application Data

[63] Continuation-in-part of Ser. No. 70,851, Aug. 29, 1979, abandoned.

[51] Int. Cl.³ .............................. A61F 1/20; G10I 1/10
[52] U.S. Cl. ........................................ 179/1 AL; 3/1.3
[58] Field of Search ............. 3/1.3; 179/1 AL, 121 C, 179/157

[56] References Cited

U.S. PATENT DOCUMENTS

| | | | |
|---|---|---|---|
| 1,901,433 | 3/1933 | Burchett | 3/1.3 |
| 3,066,186 | 11/1962 | Trammell | 179/1 AL |
| 3,508,000 | 4/1970 | Snyder | 179/1 AL |

FOREIGN PATENT DOCUMENTS 1247505 10/1960 France ...................................... 3/1.3

*Primary Examiner*—Ronald L. Frinks
*Attorney, Agent, or Firm*—Watts, Hoffman, Fisher & Heinke Co.

[57] ABSTRACT

An electronic artificial larynx supported and operated without the use of an operator's hands. The artificial larynx includes an electrical circuit having a signal generator and a tone generator. The tone generator is attached to and supported by a pair of eyeglasses worn by the operator. A switch for opening and closing the electrical circuit is attached to a portion of the operator's body and is actuated by movement of one of the operator's limbs relative to his torso. In a preferred embodiment, the switch is attached to an arm band and is actuated by movement of an operator's arm toward his torso.

10 Claims, 10 Drawing Figures

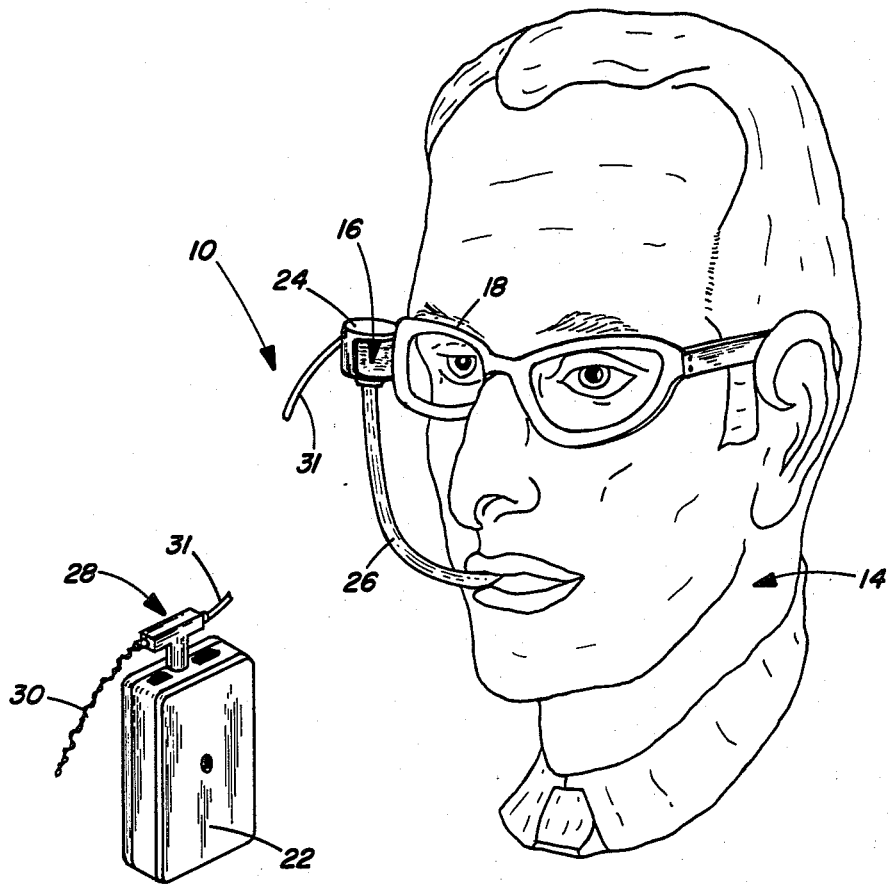
FIG. 1
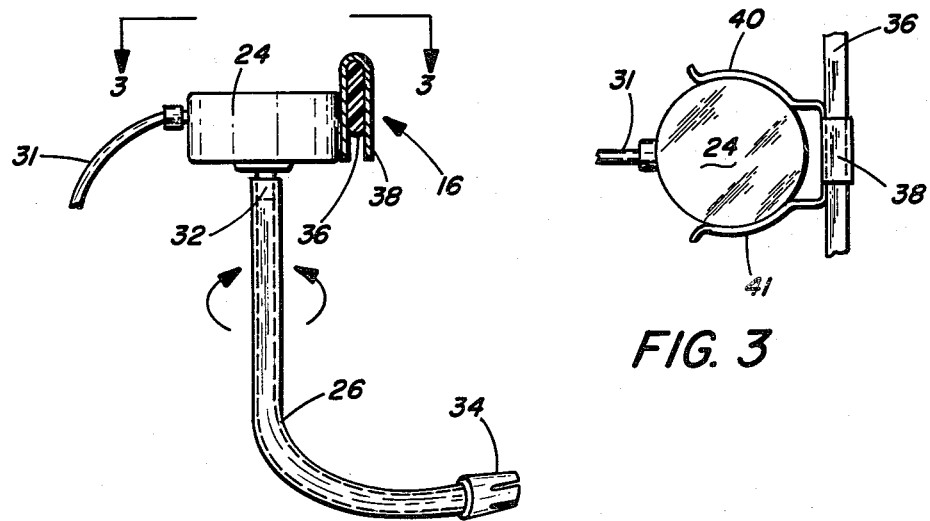
FIG. 2
FIG. 3

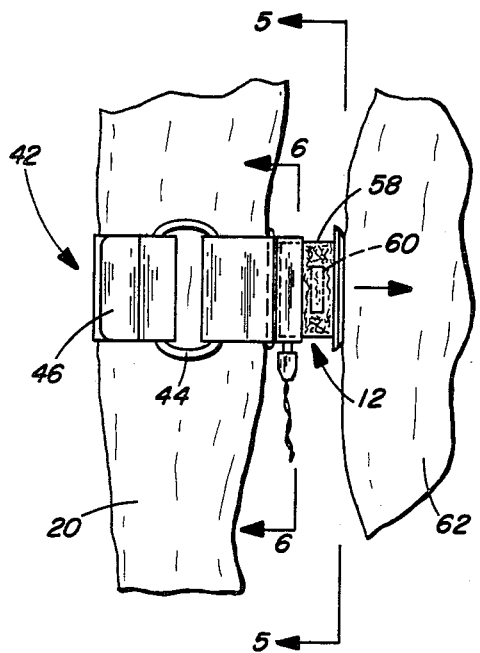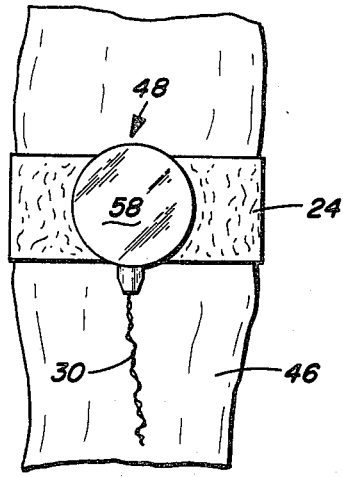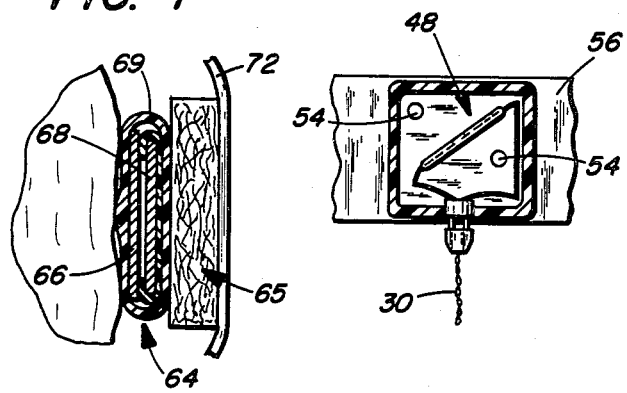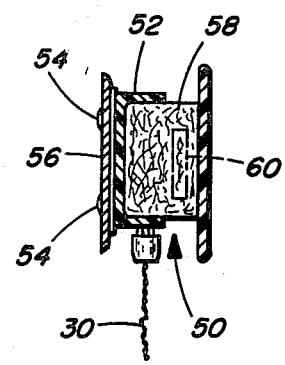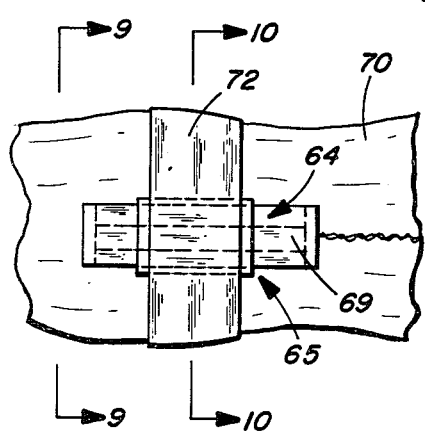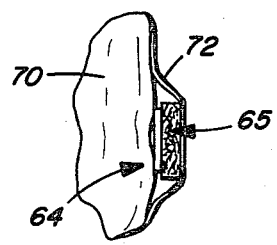

ELECTRONIC ARTIFICIAL LARYNX

CROSS-REFERENCE TO RELATED APPLICATION

This is a continuation-in-part of a United States patent application, Ser. No. 070,851, filed Aug. 29, 1979, now abandoned. That application discloses an electronic artificial larynx operated hands-free with a switch actvated by movement of the operator's forehead.

BACKGROUND OF THE INVENTION

This invention relates to switches and suppr :t assemblies for electronic artificial larynxes.

Electronic artificial larynxes are used by persons who have had their diseased larynx or "voice box" removed. Invariably, the removal causes a person to lose the power of normal articulation or speech because the person can no longer produce a tone in the throat which can be modulated in the mouth into articulate speech. In those instances, electronic artificial larynxes are useful because they provide a tone substantially resembling the tone normally produced by the natural larynx.

Prior electronic artificial larynxes have been controlled by switches, which shut off the electronic larynx to conserve a power source when the larynx is not in use. Often, the control switch was hand-operated and other parts of the electronic larynx were hand-held.

Problems arise with hand-operated or hand-supported electronic artificial larynxes when a would-be user is not able or does not desire to hold a component of the electronic larynx in his hand. This may occur when the user is physically unable to use his hands or desires to use his hands for other functions while he talks through the electronic larynx. Accordingly, it is desirable that supports and switches for electronic artificial larynxes enable the artificial larynx to be operated without use of the user's hands.

SUMMARY OF THE INVENTION

The present invention is an improved electronic artificial larynx that meets the above needs. Basically, an artificial larynx of the present type includes a tone generator, a mouth tube for the tone generator through which a tone can be transmitted to an operator's mouth, and an electrical circuit that includes a signal generator for operating the tone generator and a control switch for operating the signal generator. The present improved artificial larynx includes a clamp connecting the tone generator and tube to a pair of eyeglasses in a manner that supports the two and locates the tube adjacent the operator's mouth. In addition, the switch is attached to the operator's body remote from the tone and signal generators and is constructed to be actuated by movement of one of the operator's limbs relative to his torso.

In the preferred embodiment of the invention, the clamp is attached to a temple piece of the eyeglasses and locates the tone generator and tube alongside the operator's head, outside the operator's normal line of sight. The switch is attached to an arm band and is actuated by movement of an operator's arm toward his torso.

By attaching the tone generator and its associated mouth tube to the eyeglasses, the tone generator and tube can be supported without the use of the operator's hands. Further, by attaching the electronic switch to the band for actuation in response to movement of an operator's limb, the switch can be supported and operated hands-free.

The above and other features and advantages of this invention will become more apparent as the invention becomes better understood from the detailed description that follows, when considered in connection with the accompanying drawings.

BRIEF DESCRIPTION OF THE DRAWINGS

FIG. 1 is a perspective view of the present invention secured to a representative user of the invention;

FIG. 2 is a fragmentary, cross-sectional view of the invention illustrated in FIG. 1;

FIG. 3 is an enlarged fragmentary view of a tone generator, clamp, and eyeglass frame illustrated in FIG. 2;

FIG. 4 is a plane view of a switch assembly for the present invention attached to an arm band;

FIG. 5 is another view of the switch assembly and arm band of FIG. 4;

FIG. 6 is an enlarged cross-sectional view of the switch taken along line 6—6 of FIG. 4;

FIG. 7 is an enlarged view of the FIG. 4 switch assembly with a portion of the switch housing broken away;

FIG. 8 is a plan view of a second switch assembly and arm band;

FIG. 9 is a fragmentary plan view taken along line 9—9 of FIG. 8; and,

FIG. 10 is a cross-sectional view taken along line 10—10 of FIG. 8.

DETAILED DESCRIPTION OF THE PREFERRED EMBODIMENTS

Referring to the drawings, an artificial electronic larynx 10 with an operating switch assembly 12 is shown in association with a representative operator or user 14 in FIGS. 1 and 4. The larynx 10 is secured by a clamp 16 to a pair of eyeglasses 18 worn by the operator. The switch assembly 12 is secured to one of the user's arms 20 for actuation by movement of that arm toward the user's torso. The larynx includes a signal generator 22 connected electrically with a tone generator 24, and a mouth tube 26 attached to the tone generator and placeable in the user's mouth, to produce an audible tone which can be used by the operator 14 to produce articulate speech.

The signal generator 22 is adapted to generate electrical signals or pulses of energy representative of the plurality of frequencies contained within the complex acoustical wave of the audible tone normally developed by the natural larynx. The tone generator 24 is connected in electrical circuit to the signal generator, by a conventional T-connector 28 and electrical cables 30, 31, and is responsive to signals from the generator 22 to transform the signals into an audible tone closely resembling the normally developed tone by natural larynx. A signal generator and tone generator of this type are described in U.S. Pat. No. 3,066,186, the disclosure of which is incorporated herein by reference.

The signal generator 22 is sized to fit in a shirt pocket of the user 14 and has a clip (not shown) for securing the generator to the pocket.

The mouth tube 26 is hollow, plastic, and non-toxic. As best shown in FIG. 2, one end of the tube is rotatably connected to a stationary stem 32 of the tone generator 24. The other end of the mouth tube is for placement in the user's mouth (as shown in FIG. 1) and has a filter 34 for inhibiting entry of moisture from the mouth. The tube is used to transmit audible tones from the tone generator 24 to the user's mouth where the tones can be modulated into speech.

As best shown in FIGS. 2 and 3, the clamp 16 is attached to a temple piece 36 of the eyeglasses 18 by a U-shaped clip 38 which is inverted and press fit about the temple piece. A pair of arcuate prongs 40, 41 extend from the clip and form a contour compatible with the contour of an outer surface of the tone generator 24. The prongs 40, 41 are made of spring metal and are pushed apart from initial positions to hold the tone generator 24 between them by a spring-biased force. Since the tone generator is cylindrical and the prongs are arcuate, the tone generator can be rotated between the prongs to adjust the position of the mouth tube 26 relative to the user's mouth.

The clamp 16 locates the tone generator 24 extremely close to the temple piece 36. This results in a small moment arm between the temple piece and the center of gravity of the tone generator, which avoids distortion of the clamp by limiting the moment of force caused by the weight of the tone generator and its associated mouth tube 26.

Referring to FIG. 4, the switch assembly 12 is connected to the arm 20 by a band 42. The band supports the switch assembly and includes a latching ring 44 and an overlapping closing flap 46 whose length can be modified (the adjustability feature not shown) to adjust the circumferential size of the band. Accordingly, the band can be modified to fit securely around the arm 20 or any other of the user's limbs. A similar band can be sized to fit around another portion of the human body, such as the waist.

The switch assembly 12 includes a magnetic reed 48 and a switch actuator 50. The magnetic reed switch (best shown in FIG. 6) has a housing 52 attached to the band 42 by a pair of rivets 54 and a supporting plate 56 (see FIG. 7). The switch is connected to the T-connector 28 by cable 30 and is in a series circuit with the signal generator 22 and tone generator 24 to control electrical energization of the signal generator. The switch actuator 50 includes a compressible pad 58 and a magnet 60 carried by the pad. When the user 14 moves his arm 20 against his torso 62, the pad is compressed and the magnet is moved close to the magnetic reed switch 48. Proximity of the magnet causes the switch (which is normally opened) to become closed and thereby turns on the artificial larynx. When the user desires to shut off the larynx, he merely moves his arm away from his torso, whereupon the compressed pad expands and the magnet 60 moves away from and allows the switch 48 to open.

A second embodiment of a switch assembly is illustrated in FIGS. 8-10 and includes a pressure actuated switch 64 and a switch actuator 65. The switch 64 comprises a pair of parallel copper plates 66, 68, in an hermetic envelope 69, which are normally spaced apart by resilient material between the plates to create an open switch condition. The switch 64 is connectable to any one of the operator's limbs (here an arm 70) by a strap or band 72 having an adjustable circumference (the adjustability feature not shown). A compressible pad serves as the switch actuator 65 and is disposed between the strap 72 and the switch 64. The envelope 69 is carried by the pad. When the user 12 desires to turn on the electric larynx, he moves his arm 70 against his torso, whereupon the pad compresses, the plates 66, 68 become distorted, and the plates contact one another to close the switch 64. When the user desires to shut off the larynx, he merely moves his arm 70 away from his torso.

While the preferred embodiments of the invention have been disclosed in detail, various modifications or alterations may be made therein without departing from the spirit or scope of the invention set forth in the appended claims.

What is claimed is:

1. In an electronic artificial larynx having a mouth tube connected to a tone generator and an electrical circuit that includes the tone generator and a signal generator, the improvement comprising:
    (a) a clamp secured to the tone generator and adapted to be attached to a pair of eyeglasses;
    (b) a band adapted to be attached to a portion of a human body;
    (c) an operating switch for the electrical circuit attached to the band; and,
    (d) a switch actuator attached with the switch to the band to actuate the switch in response to movement of a limb of the body relative to the torso of the body.

2. The artificial larynx of claim 1 wherein the clamp comprises:
    (a) a clip for attachment to a temple piece of the eyeglasses; and,
    (b) a pair of arcuate prongs attached to the clip, the prongs securing the tone generator between them.

3. The artificial larynx of claim 2 wherein the clip is substantially U-shaped and is adapted for press-fit attachment to the temple piece.

4. An electronic artificial larynx comprising:
    (a) a signal generator adapted to generate electrical signals representative of the plurality of frequencies contained within the acoustical wave of the audible tone normally developed by a natural larynx;
    (b) a tone generator connected in an electrical circuit to the signal generator and responsive to the signals from the signal generator to transform the signals into an audible tone resembling the tone developed by a natural larynx; and,
    (c) clamping means for supporting the tone generator and attaching it to a pair of eyeglasses.

5. The artificial larynx of claim 4, further including a stem on said tone generator and a hollow, non-toxic plastic tube having an end rotatably connected to said stem of the tone generator and an end for placement in the mouth of a human head.

6. The artificial larynx of claim 4 wherein the clamping means comprises:
    (a) a substantially U-shaped clip for press-fit attachment about a temple piece of the eyeglasses; and,
    (b) a pair of arcuate prongs attached to the clip, the prongs being made of spring metal and being compatible to the contour of a surface of the tone generator to hold the tone generator between them by a spring-biased force.

7. An electronic artificial larynx comprising:
    (a) a signal generator adapted to generate electrical signals representative of the plurality of frequencies contained within the acoustical wave of the audible tone normally developed by a natural larynx;
    (b) a tone generator connected in an electrical circuit to the signal generator and responsive to the signals from the signal generator to transform the signals into an audible tone resembling the tone developed by a natural larynx;

(c) a band adapted to fit securely around a portion of a human body;

(d) a switch attached to the band for operating the electrical circuit; and, (e) a switch actuator to actuate the switch in response to movement of a limb of the body relative to the torso of the body.

8. The apparatus of claim 7 wherein the switch is a magnetic reed switch, and the actuator is carried by the band and comprises a magnet carried by a compressible pad.

9. The apparatus of claim 7 wherein the switch is pressure actuated and comprises two substantially parallel plates normally spaced apart by material between the plates to create an open electric circuit, wherein the material can be compressed and the plates distorted to permit contact between the two plates to create a closed electric circuit that includes the tone generator and signal generator.

10. In an electronic artificial larynx having a tone generator and a signal generator, the improvement comprising:

(a) clamping means for supporting the tone generator and attaching it to a pair of eyeglasses;

(b) a band adapted to fit securely around a human limb;

(c) a switch attached to the band for operating the artificial larynx; and, (d) a switch actuator to actuate the switch in response to movement of the limb.

* * * * *